(12) United States Patent
Henderson et al.

(10) Patent No.: US 7,442,162 B2
(45) Date of Patent: Oct. 28, 2008

(54) METHOD AND APPARATUS FOR TREATMENT PLANNING USING IMPLANTED RADIOACTIVE SEEDS

(75) Inventors: Douglass L. Henderson, Madison, WI (US); Sua Yoo, Southfield, MI (US); Michael E. Kowalok, Madison, WI (US); Bruce R. Thomadsen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 661 days.

(21) Appl. No.: 10/851,515

(22) Filed: May 21, 2004

(65) Prior Publication Data

US 2008/0242914 A1    Oct. 2, 2008

Related U.S. Application Data

(60) Provisional application No. 60/572,962, filed on May 20, 2004, provisional application No. 60/472,628, filed on May 22, 2003.

(51) Int. Cl.
*A61N 5/00* (2006.01)

(52) U.S. Cl. .......................................................... 600/1

(58) Field of Classification Search ................. 600/1–8, 600/300, 407, 425, 427, 431, 437, 439, 458; 604/19, 27–28, 48, 57, 59, 60, 62–64, 73, 604/500, 502–503, 514, 517; 702/19
See application file for complete search history.

(56) References Cited

U.S. PATENT DOCUMENTS

| | | | |
|---|---|---|---|
| 6,327,490 B1 * | 12/2001 | Spetz | 600/427 |
| 6,387,034 B1 * | 5/2002 | Lee | 600/1 |
| 6,512,942 B1 * | 1/2003 | Burdette et al. | 600/427 |
| 6,530,873 B1 * | 3/2003 | Lee | 600/1 |
| 6,539,247 B2 * | 3/2003 | Spetz | 600/427 |
| 2002/0177748 A1 * | 11/2002 | Munro, III | 600/3 |
| 2003/0130573 A1 * | 7/2003 | Yu et al. | 600/407 |
| 2004/0092786 A1 * | 5/2004 | Zaider et al. | 600/1 |
| 2004/0225174 A1 * | 11/2004 | Fuller et al. | 600/1 |

* cited by examiner

*Primary Examiner*—Samuel G. Gilbert
(74) *Attorney, Agent, or Firm*—Boyle Fredrickson, S.C.

(57) ABSTRACT

A pre-computed sensitivity function providing ex ante assessment of optimal placement of a single radioactive seed, is used for sequential placement of multiple radioactive seeds. The location of each successive seed may also be constrained by an exclusion function omitting areas in the target receiving a pre-defined dose from the preexisting seeds. This technique makes possible optimization of additional dimensions of treatment planning including using a different number of needles and using mixed seed types.

29 Claims, 10 Drawing Sheets

METHOD AND APPARATUS FOR TREATMENT PLANNING USING IMPLANTED RADIOACTIVE SEEDS

CROSS-REFERENCE TO RELATED APPLICATIONS

This application claims the benefit of U.S. provisional applications 60/472,628 filed May 22, 2003; and 60/572,962 filed on May 20, 2004, entitled Directionally Emitting Radioactive Sources for Permanent Implantation, hereby incorporated by reference.

STATEMENT REGARDING FEDERALLY SPONSORED RESEARCH OR DEVELOPMENT

This invention was made with United States government support awarded by the following agencies: DOE DE-FG07-011D14104. The United States has certain rights in this invention. Co-Inventor Michael Kowalok was supported on a DOE Fellowship Program (DOE Computational Science Graduate Fellowship Program (CSGF)). Hence, partial support for this work was provided by the DOE CSGF program

BACKGROUND OF THE INVENTION

The present invention relates to radiation therapy for the treatment of cancer and the like and, in particular, to a planning method and to an apparatus for radiation therapy using implanted radioactive sources (called seeds).

Prostate permanent implant brachytherapy is a radiation treatment technique in which radioactive sources are implanted directly into the prostate and left in place permanently. Typically 50 to 100 small radioactive sources ("seeds") are implanted near the tumorous tissue.

The seeds may be a radioactive material adsorbed onto small resin spheres contained within a titanium capsule or on the surface of a silver rod also sealed in titanium. Depending on the radionuclide used, the seeds typically have a half-life of approximately 17 to 60 days providing an average energy of emitted photons of approximately 20 to 35 keV with a commercial source strength of approximately 0.5 mCi. Typical radionuclides used are $^{125}I$ and $^{103}Pd$.

The seeds are of a size, e.g., 0.8 mm in diameter and 4.5 to 5 mm long, so that they may be implanted using a hollow needle. The needle provides a lumen 1.3 to 1.5 millimeter in diameter and about twenty centimeters long into which seeds may be inserted along with spacers controlling their separation. The loaded needle is inserted into the patient and then withdrawn while a plunger ejects the contained seeds.

Placement of the seeds, for example, for use in treatment of the prostate may be done transperineally and the needles are guided by a plate having predrilled holes on a regular grid. The depth of insertion of the needles is guided by an image obtained with a transrectal ultrasonic imaging device. In this way, seeds may be accurately placed at selected regular grid locations.

The locations of the radioactive seeds along the grid are desirably selected to provide the prescribed dose to the diseased tissue of the prostate while sparing surrounding sensitive critical tissue, for example, the urethra, and rectum. Such placement is aided by treatment planning performed before the implantation of the seeds.

In current practice, treatment planning is largely trial and error based on some simple spacing rules after an inspection of the tumor site by ultrasonic or other imaging techniques. More precise treatment planning may be obtained by a number of well known optimization processes providing mathematical simulation of a dose from a given seed pattern.

Determining the dose produced by a given pattern of seeds is a relatively straightforward process, however, the "backwards" calculation from dose to seed pattern is mathematically difficult. Such problems are typically addressed by stochastic techniques such as "simulated annealing" or by "genetic algorithms", both that perform repeated forward calculations for many possible seed patterns and then apply an objective function to the dose produced by the pattern to select the best pattern.

A deterministic approach to treatment planning is provided by the "branch and bound" method described, for example, in Treatment Planning for Brachytherapy: An Integer Programming Model, Two Computational Approaches and Experiments With Permanent Prostate Implant Planning, by Lee E. K. et al., Phys. Med. Biol. 44: 145-165 (1999), and An Iterative Sequential Mixed-Integer Approach to Automated Prostate Brachytherapy Treatment Plan Optimization, D'Souza W. D. et al., Phys. Med. Biol. 46: 297-322 (2001).

Operating on high-speed computers, these approaches may take as much as an hour to complete for a typical prostate treatment plan. Such delay requires considerable inconvenience and expense to a patient, either in waiting for the implant during the treatment planning process, or in having to return after the treatment planning session at a later date for the implanting. In the situation where the patient returns at a later date, considerable effort and time is required to realign the patient to the position the patient held during the imaging used for the treatment plan.

SUMMARY OF THE INVENTION

The present invention provides a rapid method of treatment planning for the placement of radioactive seeds. An ex-ante sensitivity function is calculated, indicating preferential locations for single radiation seeds based on the desired treatment areas. The function is "ex ante" because the function is essentially static after it is computed and is not recomputed as seeds are placed. Seeds are sequentially placed in the treatment area using the ex-ante sensitivity function and the dose is forward modeled to see if completion criteria are met. If completion criterion are not met, additional seeds are added repeating this process, however, seeds are generally not moved after they are placed. The optimization process is called "greedy" and is extremely rapid, allowing treatment planning to be conducted while the patient waits.

Specifically, the present invention provides a method of treatment planning for the placement of radioactive sources in and around a tumor. In the method which may be implemented in software, an ex-ante sensitivity function is established indicating preferential source locations. Using this ex-ante sensitivity function, a source location is selected and a total dose computed based on a source at the location selected, and sources at any previously selected locations. After the selection of each source location, the total dose for all seeds placed so far is compared to completion criteria, and if the completion criteria are not met, the previous selection steps are repeated for a new source location. Otherwise, the selected source locations are output.

Thus, it is one object of at least one embodiment of the invention to provide for an extremely rapid treatment planning that may be executed on a computer in near real time. The ex-ante sensitivity function may be substantially static and thus precomputed and stored for extremely rapid execution.

The ex-ante sensitivity function may assess a relative dose to tumorous and non-tumorous tissue of the dose pattern produced by seeds over a range of different locations in a target region. The function may be a ratio of an average dose measured over the tumorous tissue to an average dose measured over the non-tumorous tissue produced by seeds at a range of different locations in a target region.

Thus it is another object of at least one embodiment of the invention to provide a simple objective function that may be quickly computed and/or stored after computation for repeated use.

The location of seeds may be fixed after the seeds are first sequentially located.

Thus it is another object of at least one embodiment of the invention to quickly reach a solution by use of a greedy process.

The computation of the total dose may be used to define an exclusion region and the step of selecting a source location using the ex-ante sensitivity function may consider only source locations outside of the exclusion region.

Thus it is another object of at least one embodiment of the invention to avoid clustering of seeds when using a static ex-ante sensitivity function.

The exclusion region may be decreased with each additional selected source location.

Thus it is another object of at least one embodiment of the invention to promote a gradual filling in of the treatment area such as promotes homogenous radiation dose.

The seed placement may continue until a computed dose from the located seeds matches the desired dose pattern within a predetermined criterion.

Thus it is another object of at least one embodiment of the invention to provide a simple method of determining when a sufficient number of seeds have been placed.

The steps of locating the radiation seeds may be repeated with different constraints on the seed location selection process including the number of needles and different types of radioactive seeds.

Thus it is another object of at least one embodiment of the invention to provide a treatment planning method that is fast enough to allow additional dimensions of optimization to be processed.

These particular objects and advantages may apply to only some embodiments falling within the claims and thus do not define the scope of the invention.

DETAILED DESCRIPTION OF THE PREFERRED EMBODIMENT

Brachytherapy Apparatus

Figure 1:
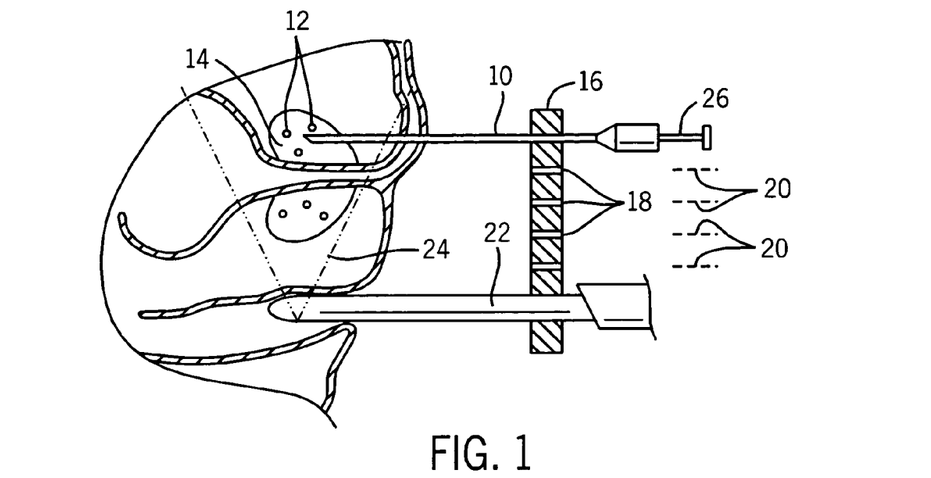
FIG. 1 is a fragmentary, cross-sectional view taken along a mid-sagittal plane of a patient receiving radioactive seeds for treatment of the prostate, such as may be guided by the present invention.

Referring now to FIG. 1, prostate brachytherapy may employ a hollow needle 10 to place radioactive seeds 12 within the prostate 14 transperineally. The needle 10 is guided by a plate 16 having a plurality of guide holes 18 placed at regular grid locations 20 over two dimensions of the plate 16.

The plate may be clamped to a transrectal ultrasonic probe 22 providing an ultrasonic beam 24 illuminating the prostate 14 so as to verify the depth of placement of the seeds 12 as they are ejected from the needle 10 by means of a plunger 26 fitting within the hollow shaft of the needle 10. The seeds 12 may be placed within the needle 10 in a preconfigured separation enforced by non-radioactive spacers.

Figure 2:
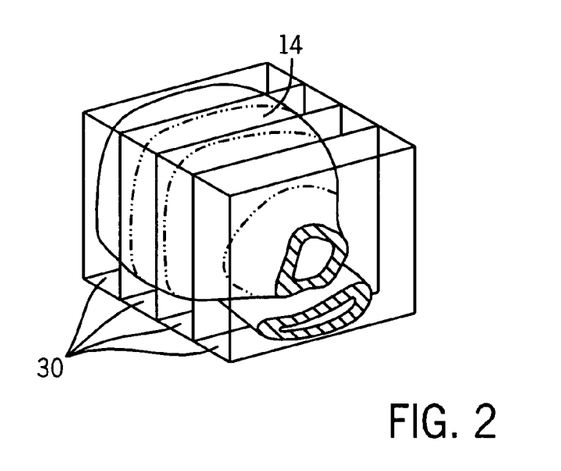
FIG. 2 is a perspective view of the prostate of FIG. 1 as divided into a series of slices that may be imaged with a transrectal probe to guide the placement of seeds.

The present invention provides a treatment planning system for prostate brachytherapy that determines where seeds 12 should be placed. Referring to FIG. 2, prior to the treatment planning, a region of interest generally including both the prostate 14 and tissue around the prostate is imaged. The images, for example, may be composed of a series of slices 30 obtained transrectally by the transrectal ultrasonic probe 22 as B-mode images. The slices 30 may be viewed individually on a screen of the ultrasound machine (not shown) or on a separate computer, either of which may be programmed to perform or assist in performing the treatment planning itself.

Figure 3:
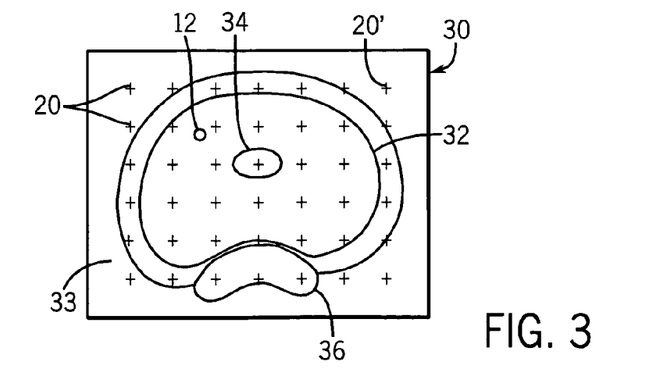
FIG. 3 is a view of one plane of FIG. 2 in which the prostate, urethra, and rectum have been outlined by a physician to show treatment regions, and further showing a grid of possible seed locations.
Figure 4:
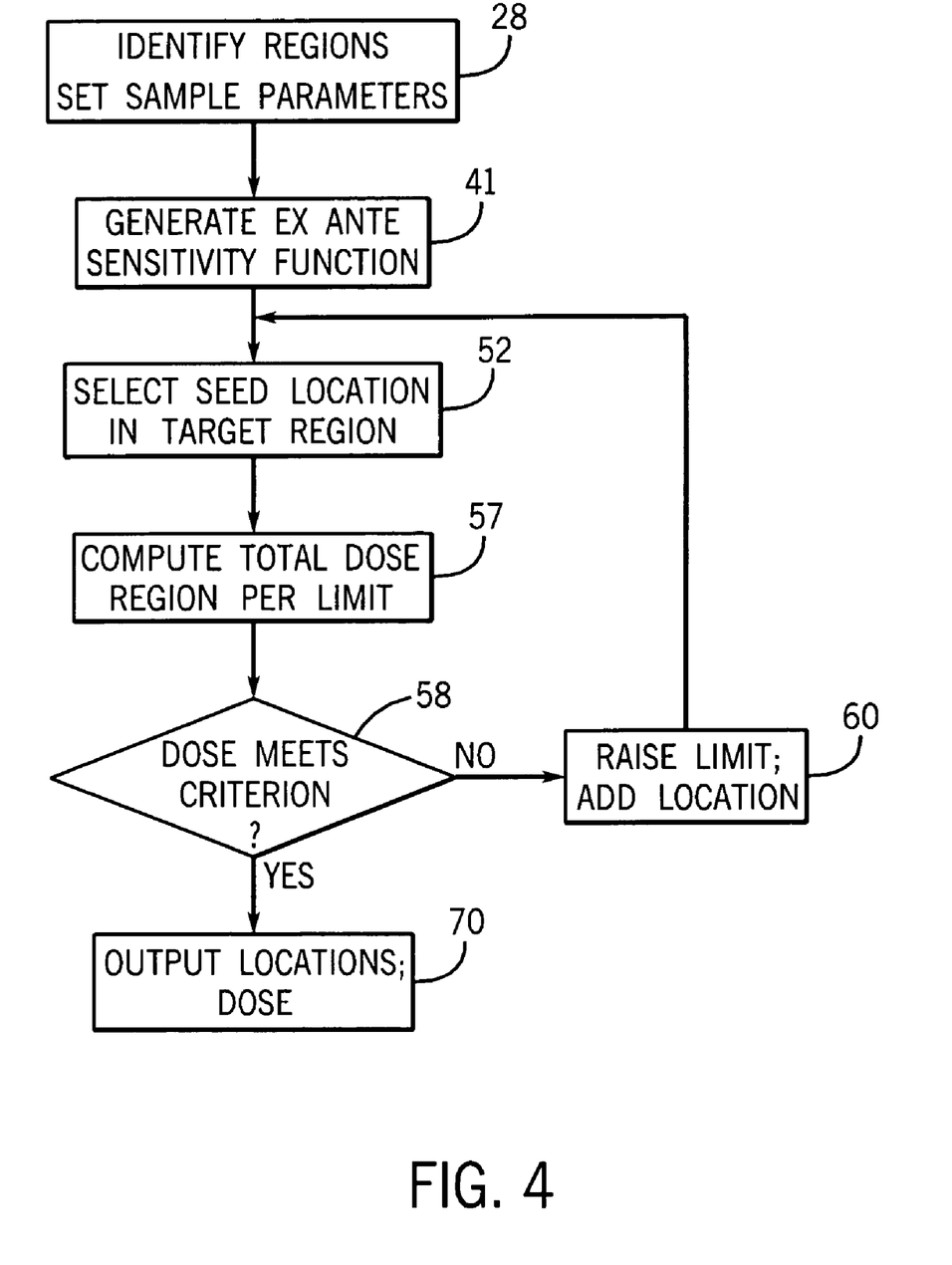
FIG. 4 is a flowchart of the method of the present invention as may be implemented in whole or in part in software.

Referring to FIGS. 3 and 4, in a first step of the treatment planning indicated by process block 28, each slice 30 may be viewed by a physician and used to identify different regions requiring different doses. In the case of the prostate, the prostate region 32 may be outlined by the physician using a cursor or similar device on a displaying ultrasound machine or terminal (not shown). Centered within the prostate region 32 is the urethral region 34, and posterior to the prostate region 32 is the rectal region 36 which may also be outlined and identified as such by the physician. The remaining tissue in this vicinity is considered margin tissue 33. Each of these regions has a volume in three dimensions as may be constructed on a slice-by-slice basis with each slice outlined by the physician.

As shown in FIG. 3, grid locations 20 are input to the computer corresponding to locations defined by the plate 16 and depths along a needle held by the plate at a location and optionally displayed. Or, as will be described below in an alternative embodiment, a range of grid location spacings, corresponding to different plates 16 may be entered with the program to select the optimum grid location spacing. Other treatment planning parameters may be entered at this time including limitations on the number of sources, the types of sources, and the number of needles as well as definitions of various functions and their parameters such as those defining the exclusion region and the ex-ante sensitivity function as will be described below, all of which may be modified by the user.

Generating an Ex Ante Sensitivity Function

Referring again to FIG. 4, once the regions have been identified and the sample parameters input per process block 28, the program pre-calculates for each region, a "sensitivity distribution" based on the particular seeds 12, the defined prostate region 32, the urethral region 34, and the rectal region 36 as indicated by process block 41. A different sensitivity distribution is established for each of the regions 32, 34, and 36 and is determined by computing the average dose value that would be received by the regions 32, 34, and 36 from a radioactive seed placed at each different grid location 20 within the area of the image of the slice 30. The average dose value can be computed using an adjoint transport calculation, or similar techniques, such as are well known in the art. Thus, for grid location 20' in the upper right-hand corner of the image of the slice 30, the height of the distribution sensitivity for the rectal region 36 would be the average dose received by all the points within the rectal region 36 from a seed 12 at grid location 20'.

The calculation of the dose used to compute the sensitivity distributions may employ a number of well-known forward dose modeling techniques and in the preferred embodiment, assumes a standard tissue characteristic for each of the regions for computational efficiency. It will be understood to those of ordinary skill in the art, however, that each of the different tissues of the different regions may be assigned different standard characteristics or the characteristics may be extracted from images of the tissues, for example, from a CT scan.

Figure 5:
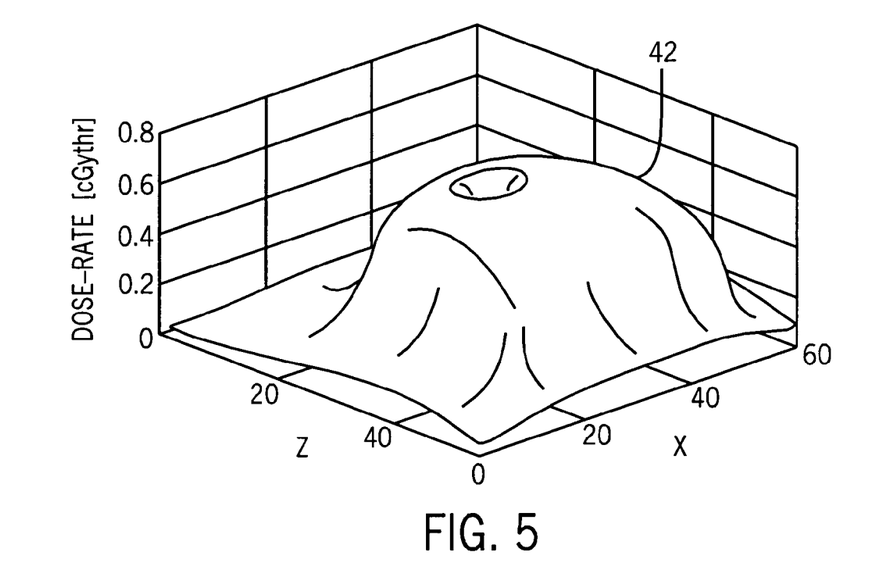
FIG. 5 is a perspective view of a three-dimensional plot of a sensitivity distribution for a slice of the prostate showing an average dose received by the prostate as a function of location for a single seed.

Referring now to FIG. 5, a sensitivity distribution 42 for the prostate region 32 intuitively shows that radioactive seeds 12 placed within the outline of the prostate have the greatest effect on its average dose. In this depiction, the height of the surface represents an average dose and the plane over which the surface lies is an x-y plane of the image of the slice 30. Multiple planes are used to define the sensitivity distribution in three dimensions.

Figure 6:
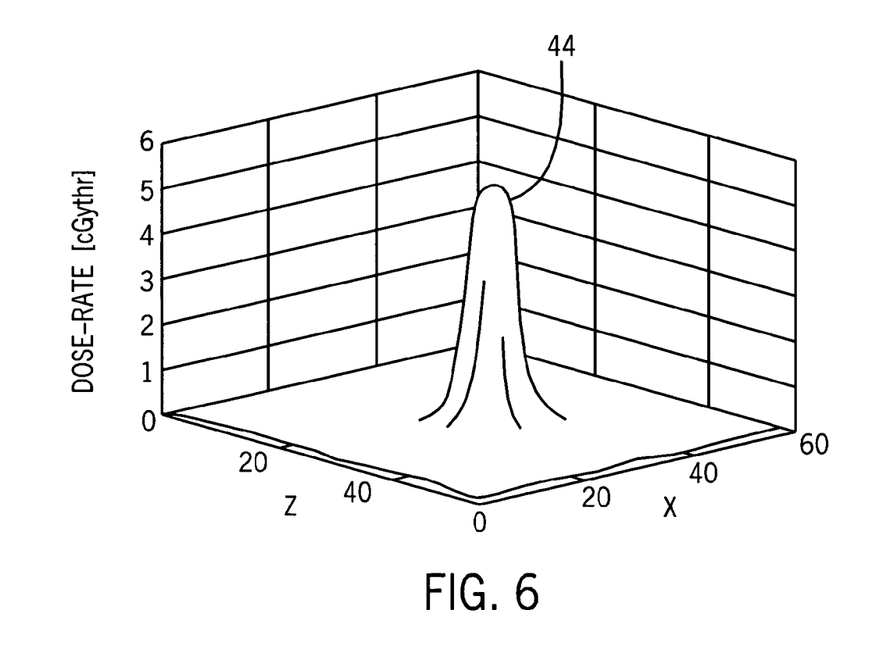
FIG. 6 is a figure similar to that of FIG. 5 showing a sensitivity distribution for the urethra.
Figure 7:
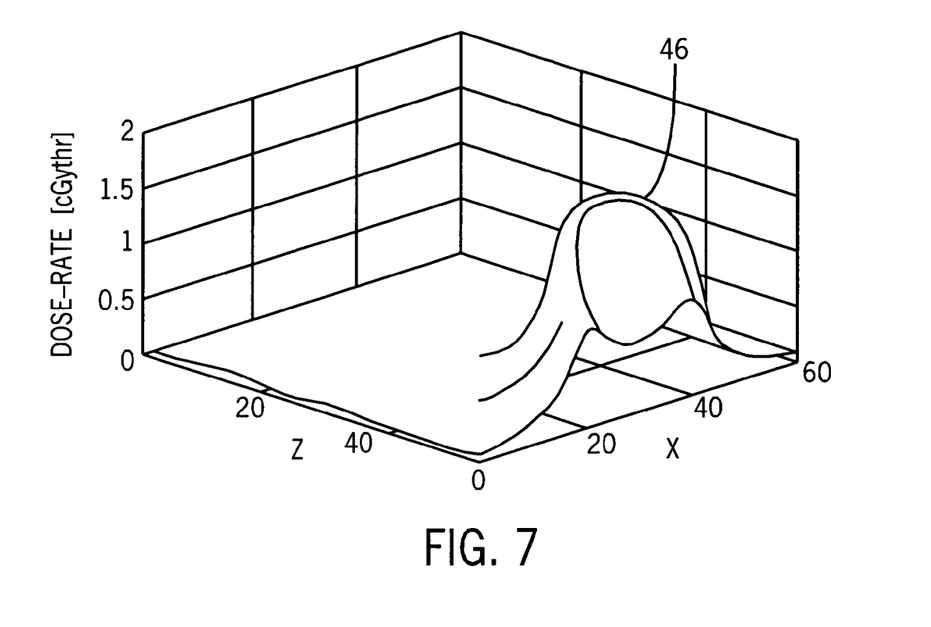
FIG. 7 is a figure similar to FIGS. 5 and 6 showing a sensitivity distribution for the rectum.
Figure 8:
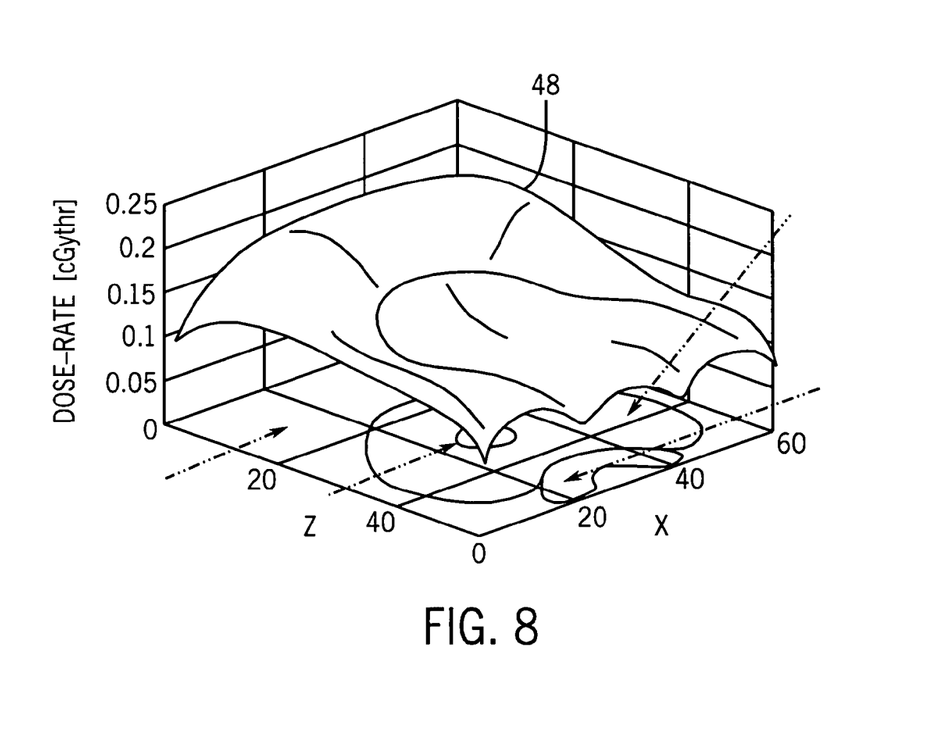
FIG. 8 is a figure similar to FIGS. 5 through 7 showing a sensitivity distribution for margin tissue outside of the prostate, rectum, and urethra.

Referring to FIG. 6 in a similar fashion, a sensitivity distribution 44 for the urethra shows that radioactive seeds 12 placed near the urethra provide the greatest average dose to the urethra. As shown in FIG. 7, a similar sensitivity distribution 46 of the rectum may be determined, having peak values in the region of the rectum, and a sensitivity distribution 48 of surrounding tissue (excluding the prostate, urethra, and rectum may be determined, per FIG. 8, showing that seed placement near the edges of the urethra or the prostate provide greatest average dose contribution to this surrounding tissue.

Figure 9:
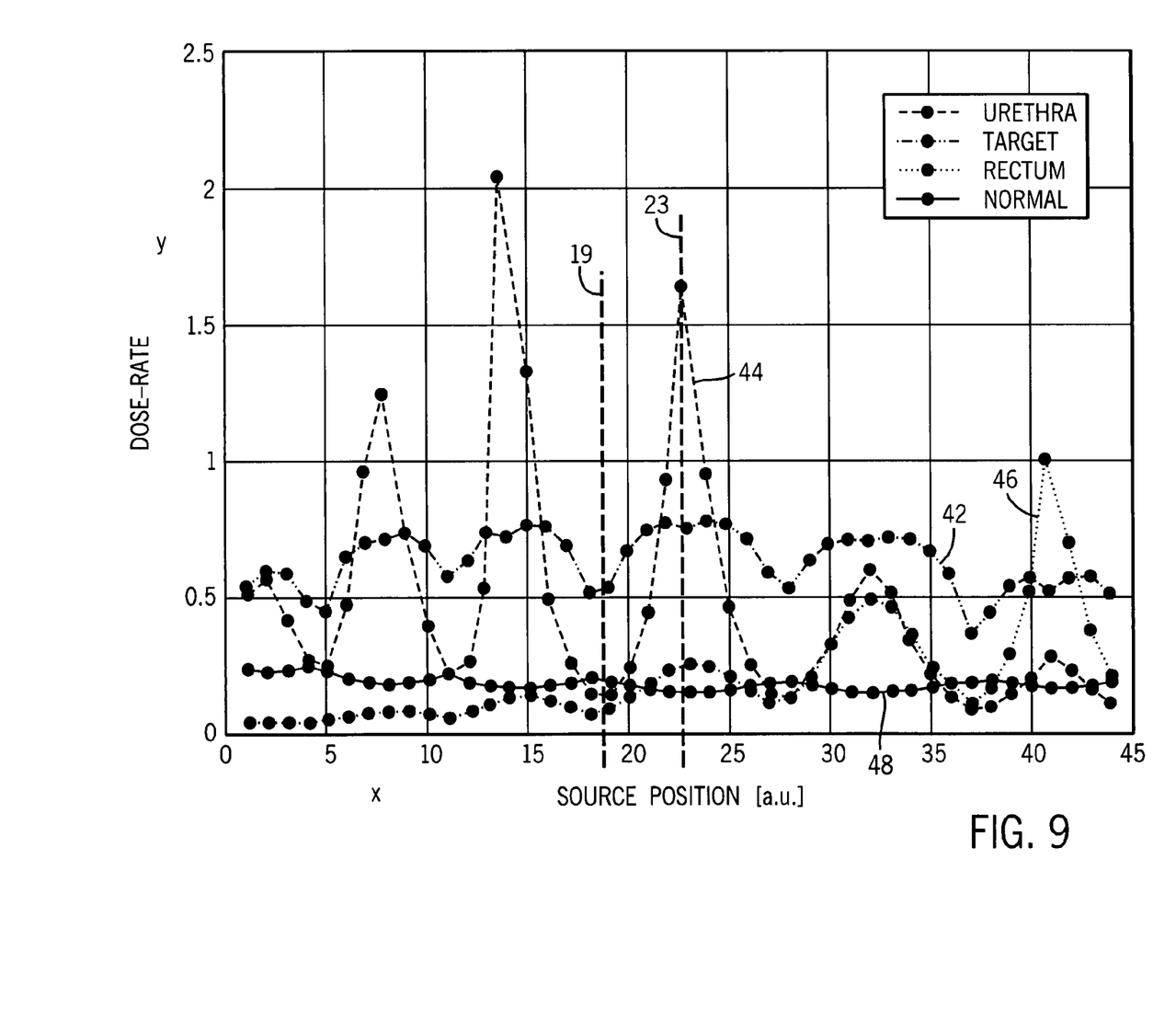
FIG. 9 is a two-dimensional plot of the sensitivity distributions of FIGS. 5 through 8, each reduced to a plot line by taking arguments along a raster pattern in the x-y plane of the corresponding ones of FIGS. 5 through 8 and showing two example locations producing high and low sensitivity for the urethra.

Referring now to FIG. 9, each of these three-dimensional surfaces of FIGS. 5 through 8 for the volume of the treatment area may be mapped to lines on a two-dimensional plot by following a raster pattern (or any systematic pattern) across the x-y plane of the sensitivity distributions of FIGS. 5 through 8 for multiple z planes. As shown in FIG. 9 at two particular locations 19 and 23, the sensitivity distributions of the various regions 32, 34, and 36 differ significantly. In this example, at location 23, being approximately centered within the image of the slice 30, the sensitivity distribution 44 for the urethra is substantially higher in value than the value of the sensitivity distribution 42 to the prostate, whereas at location 19, the sensitivity distribution 42 of the prostate is much higher than that of the sensitivity distribution 44 for the urethra. Intuitively, location 19 is a better location for a single seed 12 than is location 23.

Figure 10:
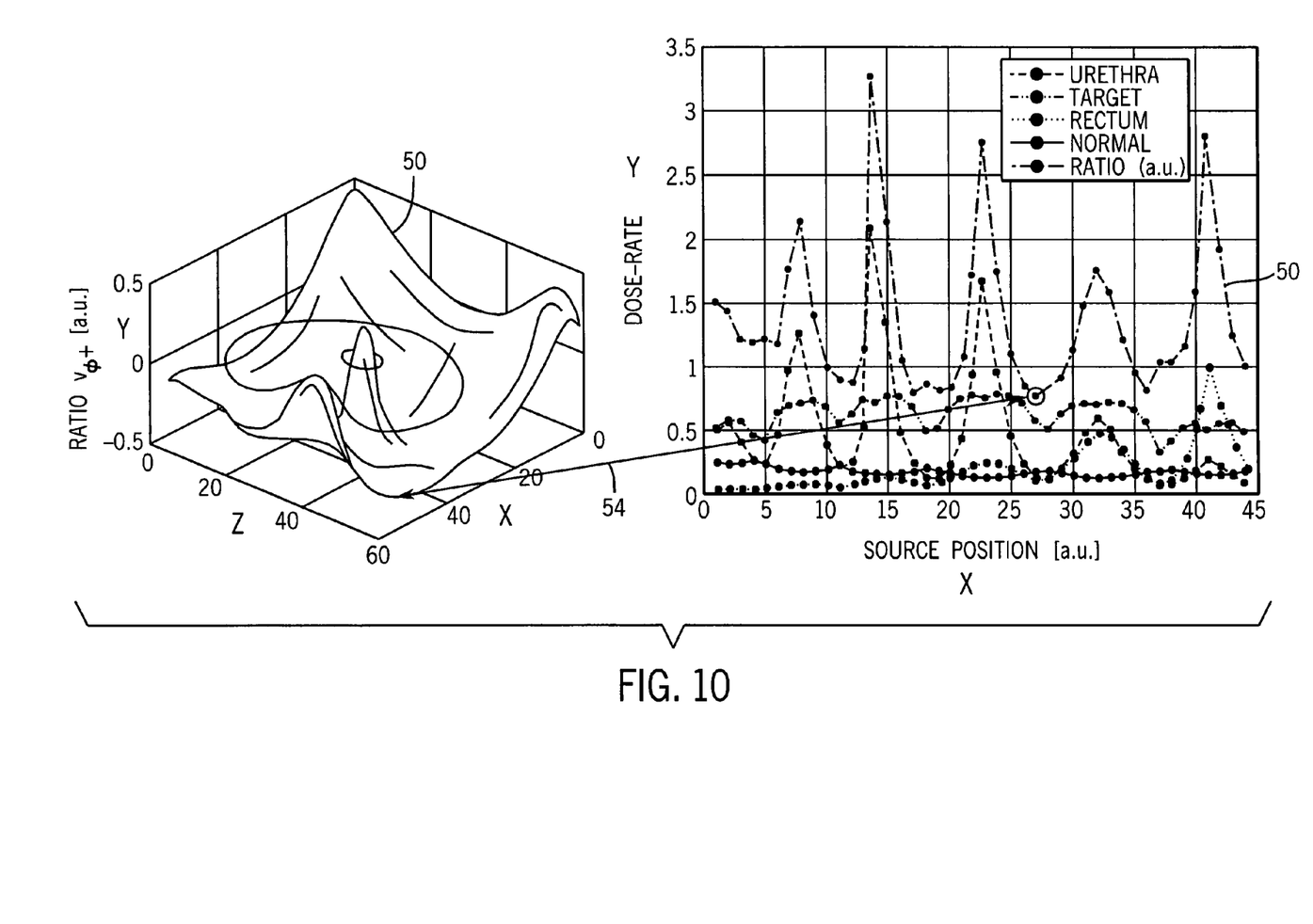
FIG. 10 is a three-dimensional and two-dimensional plot of an ex-ante sensitivity function for a slice produced by taking a ratio of the sensitivities of the various structures.

Referring now to FIG. 10, this intuitive analysis may be quantified by calculating a ratio, quantifying the relative sensitivities of the different regions according to the formula:

$$R(j) = \frac{w_{urethra} \cdot D^+_{j,urethra} + w_{rectum} \cdot D^+_{j,rectum} + w_{margin} \cdot D^+_{j,margin}}{D^+_{j,target}}$$

Where w is a weighting factor that indicates the relative importance of each region (being indicated by the subscript label urethra, etc.) and $D^+$ represents the value of the sensitivity distribution 42 for the seed location j in each of the regions.

As can be seen from inspection and reference to FIG. 9, this ratio will be small for values or locations where a radioactive seed 12 will provide proportionally more radiation to the target than to non-target tissue and larger when the non-target tissue receives greater radiation.

This ratio may be plotted to a surface shown in FIG. 10 for each z-plane where low values indicate desirable locations for a single seed 12 and forms an ex-ante sensitivity function 50 used to guide seed placement. The ex-ante sensitivity function 50 differs from an "objective" function, the latter which is usually used in iterative processes to determine how well a particular solution satisfies desired constraints. While the ex-ante sensitivity function 50 provides an indication of desirable locations for a single seed 12 because of its implicit averaging, it cannot show actual dose distribution, and thus cannot reveal the effectiveness of a set of seeds 12 in producing a given dose distribution.

Referring again to FIG. 4, this calculation of the ex-ante sensitivity function 50 is shown as process block 41 and as indicated, may be precalculated, because it remains static for the following treatment planning steps.

Determining Seed Locations

Figure 11:
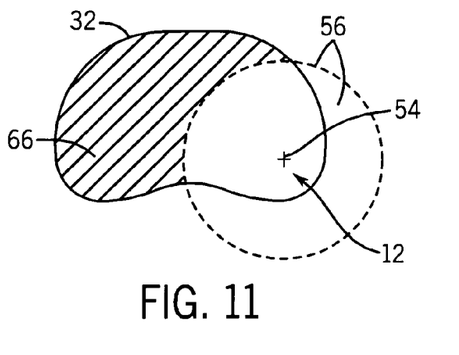
FIG. 11 is a simplified depiction of a slice of the prostate showing a first placement of a radioactive seed and the calculation of an exclusion region based on that placement.

Referring now to FIGS. 4 and 11, at a next process block 52, determination of seed locations begins with identification of a first seed location 54. This first seed location 54 may be selected by simply finding the lowest point in the surface of sensitivity function 50.

At next process block 57, this first seed location 54 is used to compute a total dose to cover the image of the slice 30 using standard forward dose modeling techniques.

At decision block 58 shown in FIG. 4, the total dose provided by the seed 12 at seed location 54 is evaluated to see whether the dose is sufficient in magnitude and coverage of the prostate region 32 to conclude the treatment planning. In the preferred embodiment, this is done simply by evaluating the total area of the prostate region 32 where the dose exceeds a predefined limit (input a process block 28) and a predetermined percentage of the area of the prostate region 32 (also input a process block 28).

In this present example, the initial limit defining the exclusion region 56 will normally be below the desired dose of the prostate region 32 and will cover less than the required area of the prostate region 32 and so treatment planning will not be complete.

On the assumption that the completion criterion has not been met, then at decision block 58, the program proceeds to process block 60 to add a new seed location. At this time, the total dose over the image of the slice 30 is used to define an exclusion region 56, shown in FIG. 11, whose boundary follows a one or more isodose line so as to embrace all regions having a dose exceeding a predetermined limit. This predetermined limit is initially set at process block 28 described above and may be determined empirically and will typically be raised at process block 60 after the first loop through process blocks 52, 57, 58, and 60.

Figure 12:
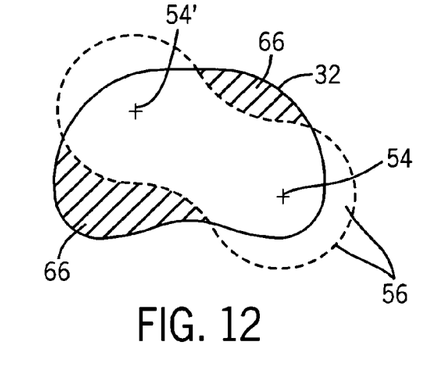
FIG. 12 is a figure similar to that of FIG. 11 showing a placement of a second radioactive seed and the resulting exclusion region.

Referring to FIGS. 4 and 12, the program then returns to process block 52 and a second seed location 54' is identified. This second seed location 54' may only be selected from a region 66 outside of the exclusion region 56 but inside the prostate region 32. Within this region 66 again, the determination of location 54' of the seed is guided by the surface of sensitivity function 50, that is, the lowest value of the objective function within regions 66 is selected with arbitrary rules being used to select among equally low values.

The program then proceeds through process block 57 and decision block 58 as before but computing total dose from seeds at both of locations 54 and 54'. At process block 60, a new exclusion region 56 is calculated as shown in FIG. 12. While the amount of total dose particularly in-between the two seed locations 54 and 54' has increased, the limit defining the exclusion region 56 has increased causing a slight shrinkage of the exclusion region around seed locations 54 increasing slightly region 66 where future seeds may be placed.

It will be understood that the exclusion region 56 as it shrinks helps prevent clustering of locations 54 providing improved homogeneity to the ultimately produced dose. This is important because, unlike iterative techniques, each seed location 54 once adopted is not changed.

Figure 13:
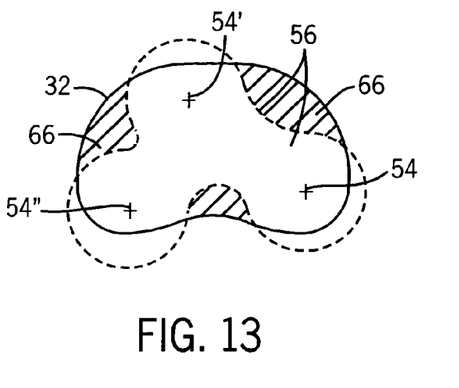
FIG. 13 is a figure similar to that of FIGS. 11 and 12 showing a placement of a third radioactive seed and the resulting exclusion region.
Figure 14:
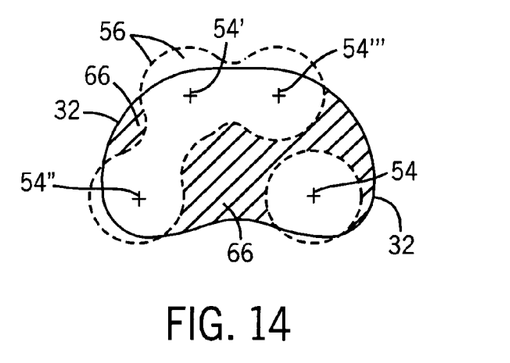
FIG. 14 is a figure similar to that of FIGS. 11-13 showing a placement of a fourth radioactive seed and the resulting exclusion region.

Referring now to FIGS. 4, 13, and 14, the process continues with additional seed locations 54'' and 54''' being added and the exclusion region 56 shrinking and better conforming to the prostate region 32 even as the dose within the prostate region 32 rises. Each time, the raising of the limit for exclusion region 56 at process block 60 shrinks, the exclusion region 56 opens up new region 66 for potential seed placement at process block 52.

Ultimately at decision block 58, the dose limit inside the prostate region 32 rises to a sufficiently high amount and the coverage of the prostate region 32 is sufficient so that the program proceeds to process block 70 which outputs desired locations of the seeds.

It will be understood that although the description above with respect to FIGS. 11 through 14 is performed on a three-dimensional data set rather than a single slice as has been shown for clarity.

Evaluating Additional Treatment Constraints

Figure 15:
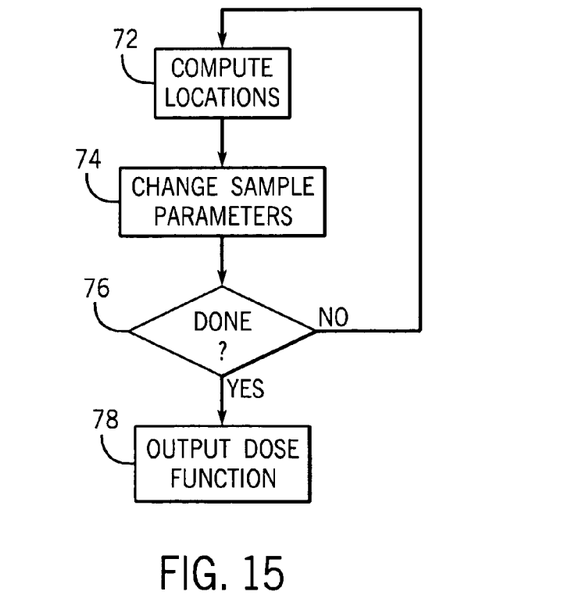
FIG. 15 is a flowchart of additional steps of the present invention for investigating different treatment parameters.

Referring now to FIG. 15, the rapid location of seeds possible with the present invention makes it possible to repeat process blocks 41, 52, 57, 58, and 60 (collectively indicated by process block 72) multiple times with slight changes in the sampling parameters previously set at process block 28 as indicated by process block 74. For example, the total number of seeds 12, a mix of different types of seeds 12, and the number of needles and/or grid locations 20 may be varied at decision block 76. The output 78 may, in this case, indicate not only the locations 54 of the seeds 12 but also a degree to which the dose criteria of decision block 58 have been met. In this way, the benefit of changes in the sample parameters may be evaluated to further optimize the radiation plan.

Figure 16:
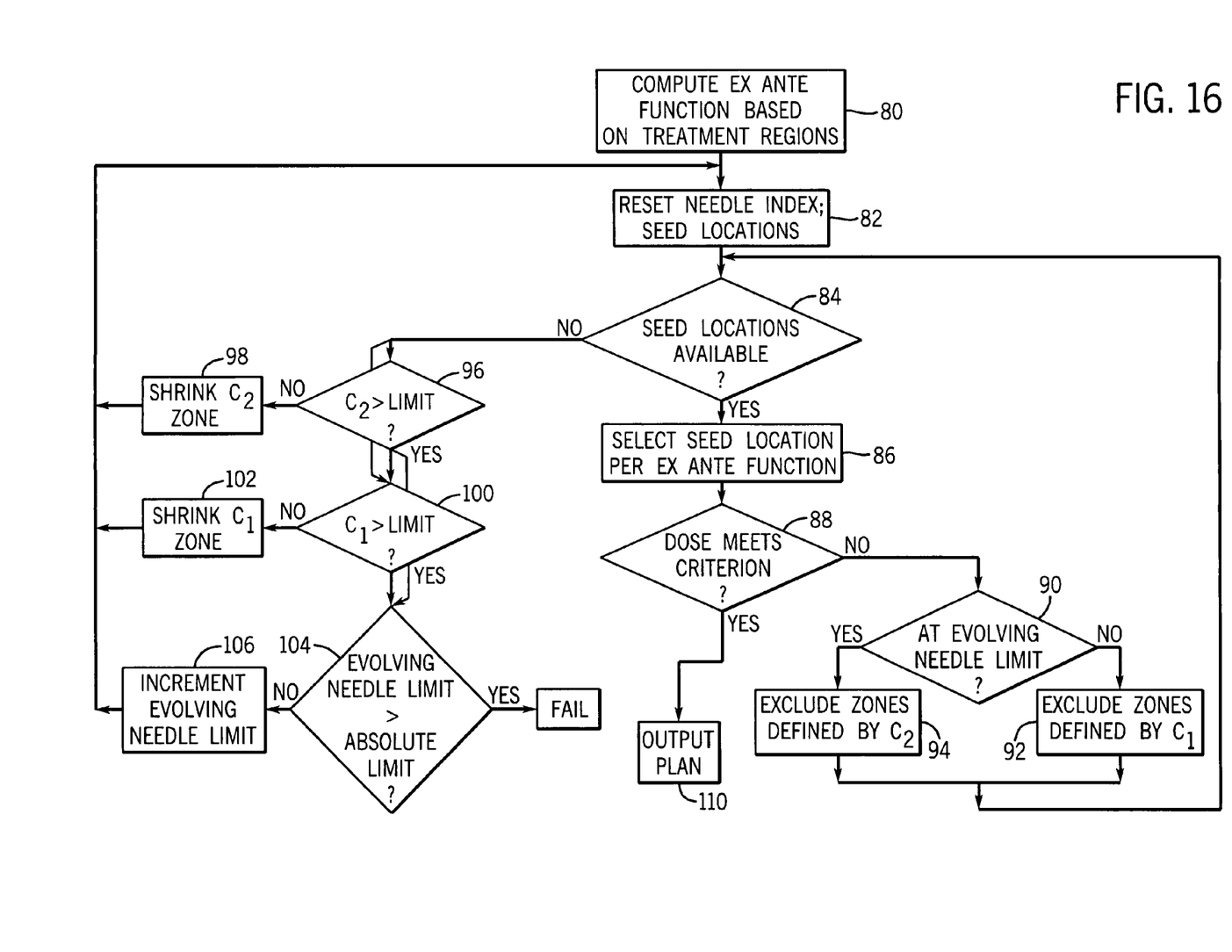
FIG. 16 is a flowchart similar to that of FIG. 4, showing the extension of the present invention for optimizing a number of needles used for the brachytherapy.

Referring now to FIG. 16, as described with respect to FIG. 4, at a first process block 80, the ex-ante sensitivity function 50 is generated based on identified treatment regions similar to that of process blocks 28 and 41 of FIG. 4.

At next process block 82, a needle-number index value N is set to zero and all seed locations 54 are reset (to a state of no seeds 12 being placed) to begin a sequential placement of seed per the ex-ante sensitivity function 50.

At succeeding decision block 84, the region 66 outside of the exclusion regions 56 but inside the prostate region 32 are examined to see if there are additional seed locations 54 that are available. Initially, there will be seed locations available, and so the program proceeds to process block 86 and a seed location is selected selecting the lowest value of the ex-ante sensitivity function 50 in region 66 as described above with respect to process block 52 of FIG. 4.

At decision block 88, the newly located seed 12 and any previously located seeds 12 since process block 82 are used to compute a total dose to the patient, and this is checked to see if it meets a predetermined criteria in a manner analogous to process blocks 57 and 58 of FIG. 4.

Initially, the few number of seeds 12 located will not meet the completion criteria, and so the program proceeds to decision block 90, one of two different exclusion zones $C_1$ or $C_2$ are used depending on how many needles have been used so far.

For the purpose of determining the exclusion zones at decision block 90, the needle-number index value N is compared to an evolving needle limit $C_{needle}$. The evolving needle limit $C_{needle}$ represents a temporary limit to the number of needles for the purpose of optimizing the number of needles. The evolving needle limit $C_{needle}$ is not reset at process block 82. Typically, the evolving needle limit $C_{needle}$ will start at a low number, say one or two needles, and be incremented up to an absolute needle limit $N_{limit}$ beyond which no additional needles will be added. Ideally, a treatment plan is obtained at an evolving needle limit $C_{needle}$ less than the absolute needle limit $N_{limit}$.

If at decision block 90, the evolving needle limit $C_{needle}$ has not been exceeded by the needle-number index value N, the program proceeds to process block 92 and exclusion zones $C_1$ are used as will be described below. Seeds 12 may be placed according to the ex ante sensitivity function 50 outside of the exclusion zones and need not be on an existing needle track. In the preferred embodiment, $C_1$ starts at 0% of the prescribed dose and is incremented by $0.1\% \times D_p$ increments as will be described below.

If at decision block 90, the evolving needle limit $C_{needle}$ has been exceeded by the needle-number index value N, the program proceeds to process block 94 and exclusion zones $C_2$ are used as will be described below. Seeds 12 may be placed according to the ex ante sensitivity function 50 only on an existing needle track. $C_2$ begins at 100% of the prescribed dose $D_p$ and is incremented by $0.1\% \times D_p$ increments as will be described below.

As has been described above, the exclusion zones defined by $C_1$ and $C_2$ describe regions within which no additional seeds 12 will be placed, each region encompassing a volume within which the dose provided by the current seeds 12 is greater than the $C_1$ or $C_2$ value. The use of two seed placement strategies with different exclusion zone definitions per process blocks 92 and 94 generally allows a first stage of free seed location up to the evolving needle limit $C_{needle}$ and thereafter a second stage of restricted seed location along existing needles to improve the dose within the needle constraint.

At the conclusion of calculation of the new exclusion zones per decision block 90 and process blocks 92 and 94, the program proceeds again to decision block 84 to see if there are still available seed locations outside of the exclusion zones as so defined.

Ultimately at decision block 84 there will be no seed locations available in the target area outside of exclusion zones. At this time, the exclusion zones are adjusted as will now be described. If the evolving needle limit $C_{needle}$ has been reached by the needle-number index value N, that is if the value $C_2$ is being used, then process block 96, the value $C_2$ is checked to see if it has exceeded a predefined limit, generally 108% of the prescribed dose $D_p$. If not, the program proceeds to process block 98 and the zone defined by $C_2$ is shrunk by increasing $C_2$ by 0.1% of the prescribed dose.

If $C_2$ is being used to define the exclusion zones and has exceeded its limit, the program proceeds to decision block 104.

Alternatively, if the evolving needle limit $C_{needle}$ has not been reached by the needle-number index value N, that is if the value $C_1$ is being used, then process block 96, the value $C_1$ is checked to see if it has exceeded a predefined limit, generally being a minimum average dose to the entire target by a single source times the number of sources. If this limit has not been reached, then the program proceeds to process block 102 and $C_1$ is increased by 0.1% of $D_p$, effectively shrinking the exclusion zone defined by $C_1$.

If $C_1$ is being used to define the exclusions zones and has exceeded its limit, per decision block 100, the program proceeds to decision block 104.

At decision block 104, if the relevant exclusion zone defined by either $C_1$ or $C_2$ is at its limit (e.g. is as small as possible) and there are no seed locations, then at decision block 104 and the evolving needle limit $C_{needle}$ is checked against an absolute limit, typically 40 needles. If the evolving needle limit $C_{needle}$ is lower than the absolute limit, then at process block 106, the evolving needle limit $C_{needle}$ is incremented. Otherwise the treatment plan fails and a new set of constraints must be considered.

It will be understood that the evolving needle limit $C_{needle}$ is increased only if no dose meeting the criteria of decision block 88 has been found. If a dose meeting the criteria of decision block 88 is found, the seed locations 54 and needle number is output at process block 110 for the lowest number of needles necessary. Thus, the general effect of the flowchart of FIG. 16 is to find the minimum number of needles that will meet the dose criteria.

Figure 17:
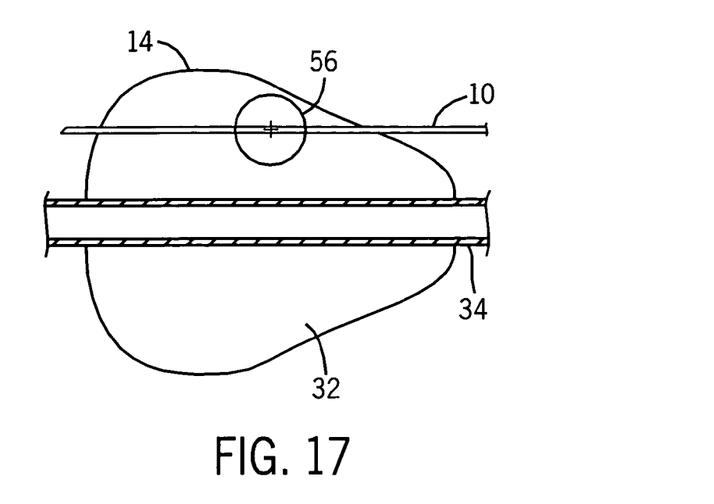
FIG. 17 is a side elevational cross-section of the prostate of FIG. 2, showing the exclusion zone of FIGS. 11 through 14 in a third dimension of needle depth and showing a needle track used in the flowchart of FIG. 6.

Referring now to FIG. 17, the sensitivity function 50 is generally three-dimensional, and the exclusion regions 56, accordingly, define exclusions both along the track of the needle 10 as shown in FIG. 17 and about the track of the needle as shown in FIGS. 11 through 14. The three-dimensional quality of the sensitivity distribution simply requires that the raster unwrapping per FIG. 10 be continued through three dimensions in a raster-like manner.

Figure 18:
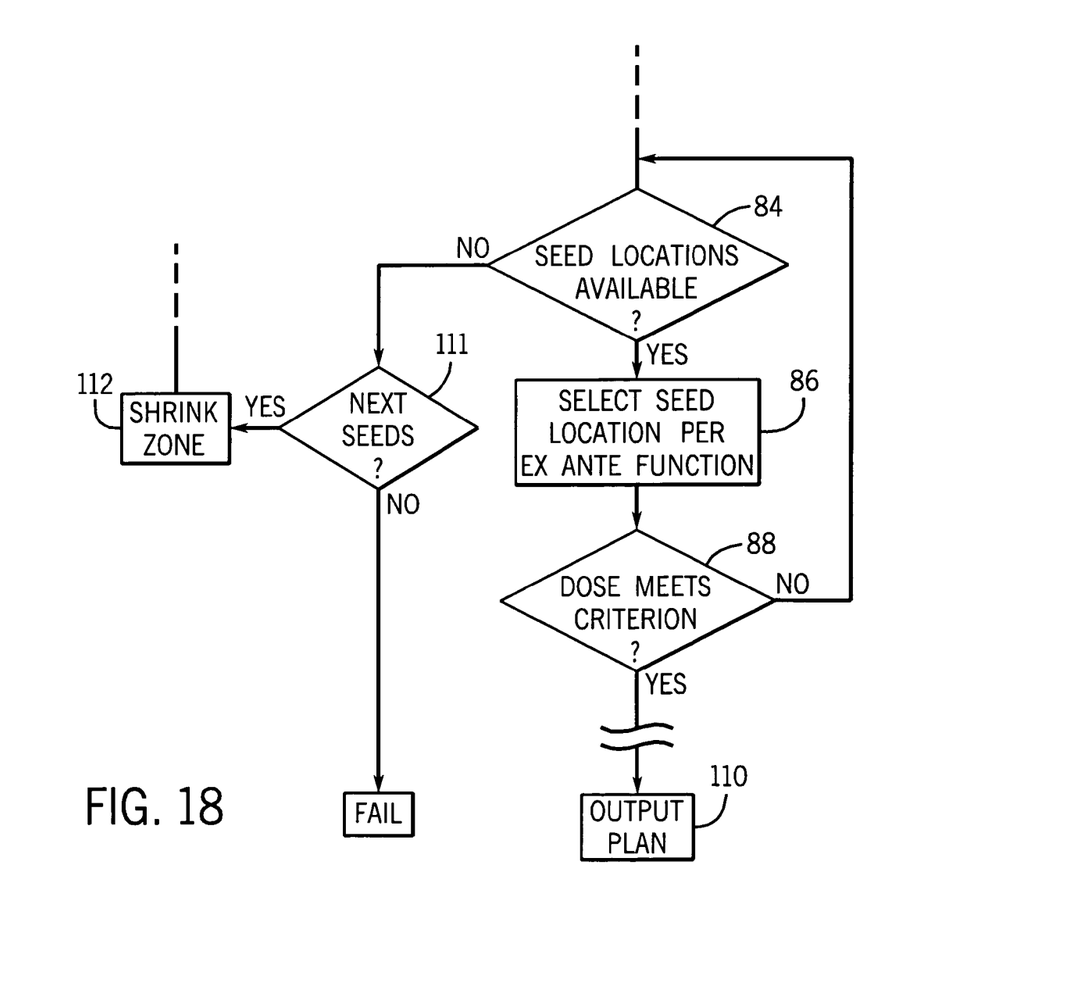
FIG. 18 is a fragmentary portion of FIG. 16, altered for optimizing two species of radioactive seeds being either of different strength or having different dose symmetries.

Referring now to FIG. 18, an approach similar to that described in FIG. 16 may be used to optimize a treatment plan for two or more different species of radioactive seeds 12, for example, high and low energy seeds 12 and 12'. In this case, assuming that needle numbers are not also optimized, process blocks 90, 94 and 92 are eliminated and a first large exclusion zone is used for the placement of the high energy seeds 12 using the procedure described above. As the high energy seeds 12 are placed at decision block 88, if a dose from currently placed seeds 12 meeting the criteria of decision block 88 has not been reached, the program loops directly back to the top of decision block 84.

If at decision block 84, no seed locations are available outside of the large exclusion zones associated with the high energy seeds 12, then the program moves to process block 111 to see if low energy seeds 12' are available. If so, at process block 112, seed size is switched to the low energy seeds and the exclusion zones are reduced correspondingly, to open up new locations for the low energy seeds.

Figure 19:
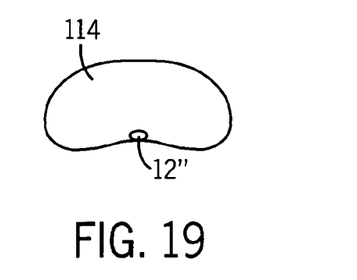
FIG. 19 is an exclusion zone similar to those of FIGS. 11 through 14 for a directional radioactive seed.
Figure 20:
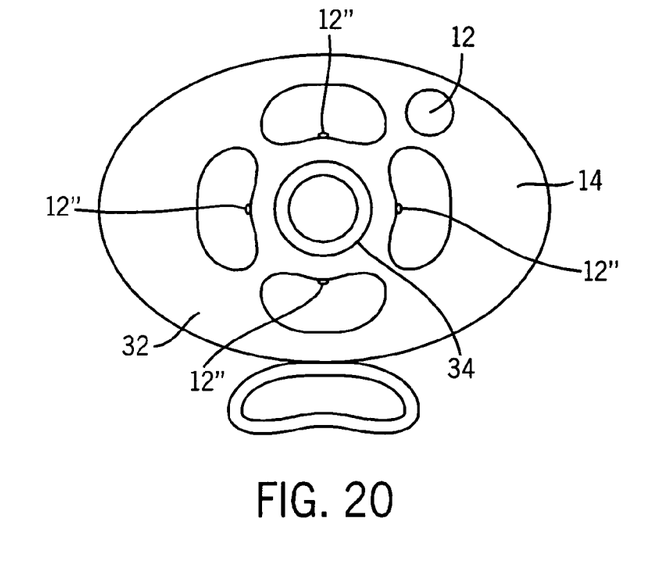
FIG. 20 is a placement pattern showing a mixing of directionally emitting and symmetrical emitting seeds per the flowchart of FIG. 18.
Figure 21:
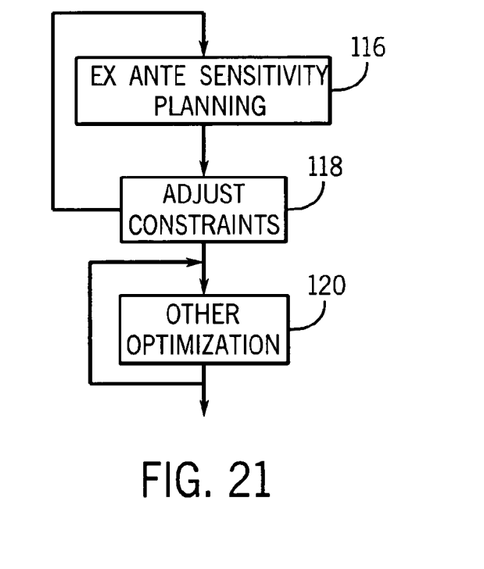
FIG. 21 is a top-level flowchart showing integration of the present algorithm with other optimization techniques.

Referring to FIG. 19, seeds 12 may vary from each other not only by being of low and high energy but by their patterns of radiation emission. Co-pending provisional application entitled: "Directionally Emitting Radioactive Sources for Permanent Implantation" filed May 20, 2004, assigned to the same assignee as the present invention, and hereby incorporated by reference, describes a method of creating seeds 12" having a directional dose pattern 114. This dose pattern 114 may be used as the basis for describing an exclusion zone so that seeds 12" having a directionally asymmetrical dose pattern may be used with regular seeds 12 in the above-described method.

In an alternative embodiment, seeds 12" may be manually or automatically located at a boundary between tissue to be treated (e.g., the prostate region 32) and tissue not to be treated 32 (e.g., the urethral region 34), arranged so that their dose pattern 114 spreads away from the tissue not to be treated. The optimization technique of FIG. 18 may then be used to add additional regular seeds 12, shrinking the exclusionary zones for all seeds as additional seeds 12 are added.

Generally, the present invention which provides a greedy heuristic 116 and is described generally with respect to FIG. 4 which may be used as part of a larger optimization system, for example, by following it with a constraint varying block 118, for example, changing numbers of needles or types of seeds per FIGS. 16 and 18, allowing the speed improvement obtained by the heuristic 116 to allow additional dimensions of optimization to be explored. The present invention may also be used with other optimization techniques 120, taking as a starting point the optimization provided by the greedy heuristic 116 and employing other techniques, such as "simulated annealing" or the like to further refine seed locations 54.

The speed advantages provided by the present invention make real-time treatment planning possible in which the patient is positioned, for example, on a treatment table and scanned in a CT machine or the like, and then, while maintaining registration with the scanning table, is treated using a treatment plan developed from the present invention without repositioning of the patient. In this case, the grid plate 16 of FIG. 1 may be attached to the scanning table.

It is specifically intended that the present invention not be limited to the embodiments and illustrations contained herein, but include modified forms of those embodiments including portions of the embodiments and combinations of elements of different embodiments as come within the scope of the following claims.

We claim:

1. A method of treatment planning for placement of radioactive seeds in a tumor in a region of a body comprising the steps of:
    (a) determining a desired dose pattern within the region of the body;
    (b) pre-calculating a sensitivity function indicating a preferred ranking of seed locations for a range of locations within the region of the body based on dose patterns produced by at least one seed moved throughout the range of different locations in a target region;
    (c) identifying a seed location outside of an exclusion zone, if any, at a location according to the preferred ranking that best contributes to the desired dose pattern;
    (d) placing the seed at that location in a treatment plan;
    (e) determine if the seeds placed in the treatment plan in total provide the desired dose pattern within a predetermined tolerance and if so concluding the treatment planning process with a current treatment plan, and if not proceeding to step (f); and
    (f) define an exclusion region about the seeds currently located in the treatment plan based on a radiation level produced by the seeds and return to step (c).

2. The method of claim 1 wherein the sensitivity function assesses a relative dose to tumorous and non-tumorous tissue of the dose pattern produced by seeds over the range of different locations in the target region.

3. The method of claim 2 wherein the sensitivity function is a ratio of an average dose measured over the tumorous tissue to an average dose measured over the non-tumorous tissue produced by seeds at the range of different locations in the target region.

4. The method of claim 1 wherein the location of seeds in the treatment plan does not change after the seeds are first located.

5. The method of claim 1 wherein a size of the exclusion zone about each seed is reduced as additional seeds are located.

6. The method of claim 1 wherein the sensitivity function is three-dimensional and the seeds are placed variably in three dimensions.

7. The method of claim 1 wherein step (c) identifies seed locations only within a predefined number of needle tracks; and
    further including the step
    (g) repeating steps (c)-(g) for increasing predefined numbers of needle tracks up to a predetermined limit and outputting one treatment plan having a fewest number of needle tracks.

8. The method of claim 7 wherein step (c) adds needle tracks as necessary until the predefined limit of needle tracks is reached and then locates seeds only along established needle tracks.

9. The method of claim 8 wherein different exclusion zones are used for locating seeds before and after the predefined number of needle tracks is reached.

10. The method of claim 1 further including the step of:
    (g) repeating steps (c)-(f) for two different types of seeds having different dose patterns starting with a first seed type and proceeding to a second seed type.

11. The method of claim 10 wherein the first seed type has a substantially different dose pattern than the second seed type.

12. The method of claim 11 wherein each first seed type is placed sequentially according to the sensitivity function outside of first exclusion zones around previously placed first seed types and second seed types are placed only after no more first seed types can be placed outside of the first exclusion zones.

13. The method of claim 11 wherein the first seed type has a directional asymmetrical dose pattern and the second seed type has a symmetrical dose pattern.

14. The method of claim 13 wherein the first seed types are placed preferentially near boundaries of the target region.

15. The method of claim 1 further including the steps of positioning a patent for treatment and obtaining treatment images to determine the desired dose pattern; and
    wherein the treatment plan is used for implanting seeds in a patient without repositioning the patient from a time of obtaining the treatment images.

16. Treatment planning software for a placement of radioactive seeds in a tumor in a region of a body, the treatment planning software on a tangible computer-readable medium executable on an electronic computer to perform the steps of:
    (a) determining a desired dose pattern within the region of the body;
    (b) pre-calculating a sensitivity function indicating a preferred ranking of seed locations for a range of locations within the region of the body based on dose patterns produced by at least one seed moved throughout the range of different locations in a target region;
    (c) identifying a seed location outside of an exclusion zone, if any, at a location according to the preferred ranking that best contributes to the desired dose pattern;
    (d) placing the seed at that location in a treatment plan;
    (e) determine if the seeds placed in the treatment plan in total provide the desired dose pattern within a predetermined tolerance and if so concluding the treatment planning process with a current treatment plan, and if not proceeding to step (f); and
    (f) define an exclusion region about the seeds currently located in the treatment plan based on a radiation level produced by the seeds and return to step (c).

17. The software of claim 16 wherein the sensitivity function assesses a relative dose to tumorous and non-tumorous tissue of the dose pattern produced by seeds over the range of different locations in the target region.

18. The software of claim 17 wherein the sensitivity function is a ratio of an average dose measured over the tumorous tissue to an average dose measured over the non-tumorous tissue produced by seeds at the range of different locations in the target region.

19. The software of claim 16 wherein the location of seeds in the treatment plan does not change after the seeds are first located.

20. The software of claim 16 wherein a size of the exclusion zone about each seed is reduced as additional seeds are located.

21. The software of claim 16 wherein the sensitivity function is three-dimensional and the seeds are placed variably in three dimensions.

22. The software of claim 16 wherein step (c) identifies seed locations only within a predefined number of needle tracks; and further including the step
(g) repeating steps (c)-(g) for increasing predefined numbers of needle tracks up to a predetermined limit and outputting one treatment plan having a fewest number of needle tracks.

23. The software of claim 22 wherein step (c) adds needle tracks as necessary until the predefined limit of needle tracks is reached and then locates seeds only along established needle tracks.

24. The software of claim 23 wherein different exclusion zones are used for locating seeds before and after the predefined number of needle tracks is reached.

25. The software of claim 16 further including the step of:
(g) repeating steps (c)-(f) for two different types of seeds having different dose patterns starting with a first seed type and proceeding to a second seed type.

26. The software of claim 25 wherein the first seed type has a substantially different dose pattern than the second seed type.

27. The software of claim 26 wherein each first seed type is placed sequentially according to the sensitivity function outside of first exclusion zones around previously placed first seed types and second seed types are placed only after no more first seed types can be placed outside of the first exclusion zones.

28. The software of claim 26 wherein the first seed type has a directional asymmetrical dose pattern and the second seed type has a symmetrical dose pattern.

29. The software of claim 28 wherein the first seed types are placed preferentially near boundaries of the target region.

* * * * *